United States Patent [19]
Mauch

[11] Patent Number: 5,514,170
[45] Date of Patent: May 7, 1996

[54] COLD PACK DEVICE

[76] Inventor: Rose M. Mauch, 1010 E. Whipp, Centerville, Ohio 45459

[21] Appl. No.: 296,021

[22] Filed: Aug. 25, 1994

[51] Int. Cl.$^6$ .................................................. A61F 7/00
[52] U.S. Cl. .......................... 607/109; 607/112; 607/114; 607/111; 126/204; 62/530
[58] Field of Search .................... 607/108–112, 114; 126/204; 383/901; 62/530; 165/46

[56] References Cited

U.S. PATENT DOCUMENTS

| | | | |
|---|---|---|---|
| 4,243,041 | 1/1981 | Paul | 128/402 |
| 4,676,247 | 1/1987 | Van Cleve | 607/112 |
| 4,776,042 | 10/1988 | Hanson | 2/7 |
| 5,020,536 | 6/1991 | Keen | 128/402 |
| 5,020,711 | 6/1991 | Kelley | 607/114 |
| 5,074,300 | 12/1991 | Murphy | 383/901 |
| 5,088,487 | 2/1992 | Turner | 62/530 |
| 5,109,841 | 5/1992 | Hubbard et al. | 383/901 |
| 5,119,513 | 6/1992 | McKay | 2/181 |
| 5,129,391 | 7/1992 | Brodsky et al. | 128/380 |
| 5,215,080 | 1/1993 | Thomas et al. | 607/112 |
| 5,305,470 | 4/1994 | McKay | 2/7 |
| 5,353,605 | 10/1994 | Naaman | 607/109 |

Primary Examiner—Angela D. Sykes
Assistant Examiner—Robert L. Nasser, Jr.
Attorney, Agent, or Firm—R. William Graham

[57] ABSTRACT

The present invention is directed to a cold pack device which includes a cold pack, a band member configured to extend around a part of a body in a self-supporting manner, and a housing connected to the band which removably receives the cold pack therein and a method of cooling using the same.

15 Claims, 3 Drawing Sheets

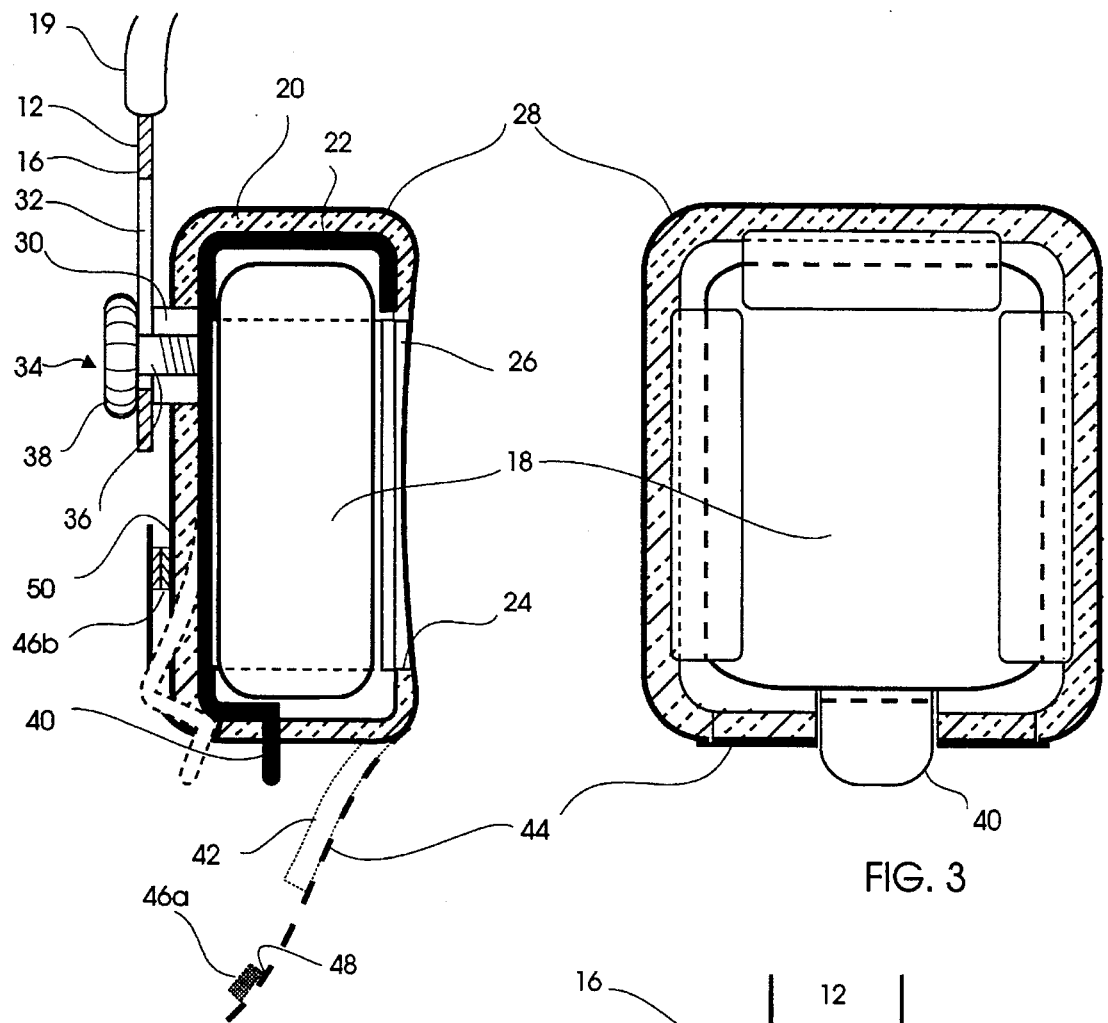
FIG. 2
FIG. 3
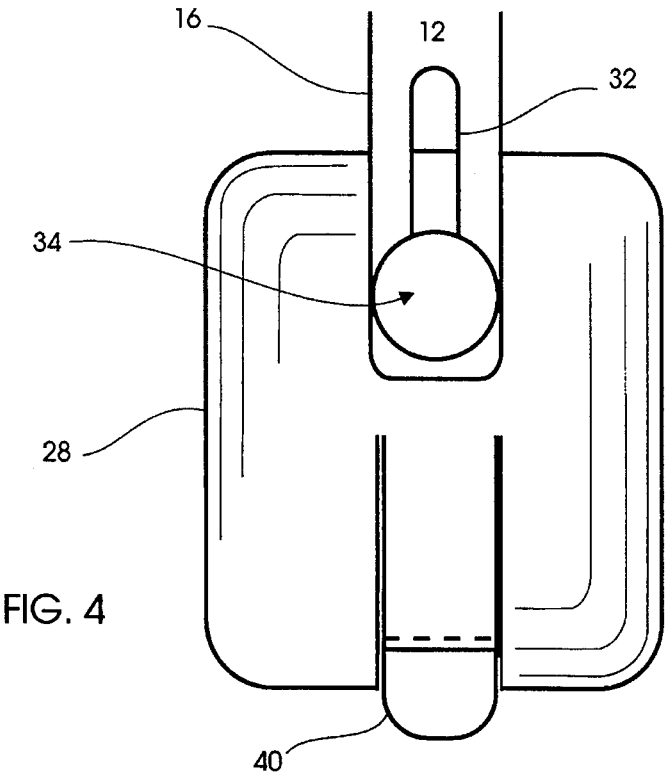
FIG. 4

COLD PACK DEVICE

BACKGROUND OF THE INVENTION

1. Field of the Invention

The present invention relates to cold packs intended to be used in hot temperature conditions, during heavy work or exercise. More particularly, but not way of limitation, the present invention relates to a cold pack device which is configured to be worn upon a person's head or additionally in combination with other cold pack device worn about the person's upper arms.

2. Brief Description of the Related Art

There exists a number of cooling devices which include, for example, a plastic bag filled with a freezable liquid or gel. Such a cold pack is used in various therapeutic applications, as well as situations wherein overheating of an individual occurs during exercise or on hot and/or humid days. The relevant art, however, employs devices which, when warmed to a point such that their effective cooling become minimal to the wearer, must be taken off and refrigerated in order to become useful again. Another disadvantage of the prior devices is that they are often of a configuration or design which causes discomfort to the wearer. For example, the cold pack is directly applied to the skin and/or the straps holding the cold pack in place are cumbersome and uncomfortable.

SUMMARY OF THE INVENTION

An object of the present invention is to cool an individual using a cold pack(s) in a comfortable manner.

Yet another object of the present invention is to maximally cool an individual using relatively few cold packs in a comfortable manner.

Still another object is to provide a cold pack device which allows for substantially continuous cooling.

Another object is to provide for a cold pack device which is readily adjustable to accommodate various sizes.

Accordingly, the present invention is directed to a cold pack device which includes a cold pack, a band member configured to extend around a part of a body in a self-supporting manner, and a housing connected to the band which removably receives the cold pack therein. In one embodiment, the band is resilient, generally u-shaped and configured to pressure fit about the head. Also, a plurality of housings are provided on the band, each having a cold pack therein and slidably fixably connected to ends of the band to permit adjusting and fixable positioning thereof. The housing includes an insulating member, a portion of which has an opening to permit thermal transfer thereacross.

In another embodiment, the band is designed to fasten to itself by Velcro® or buckle, for example. The band is of a flexible and readily conformable material.

Also, a method of cooling oneself is provided which comprises the steps of positioning a cooling device below the earlobe, about the jaw-line approximate the neck, and concurrently positioning another cooling device adjacent an inner upper arm surface of an arm.

Still other objects, advantages and novel features of the invention will be set forth in part in the description which follows and in part will become apparent to those skilled in the art upon examination of the following or may be learned by practice of the invention. The objects and advantages of the invention may be realized and obtained by means of instrumentalities and combinations particularly pointed out in the appended claims.

BRIEF DESCRIPTION OF THE DRAWINGS

FIG. 2 is a cross-section of a part of an embodiment of the cold pack device shown in FIG. 1;

FIG. 3 is a cross-section of the cold pack device of FIG. 2;

FIG. 4 is an end view of a part of embodiment in FIG. 2 of the present invention;

DETAILED DESCRIPTION OF THE PREFERRED EMBODIMENTS

Figure 1:
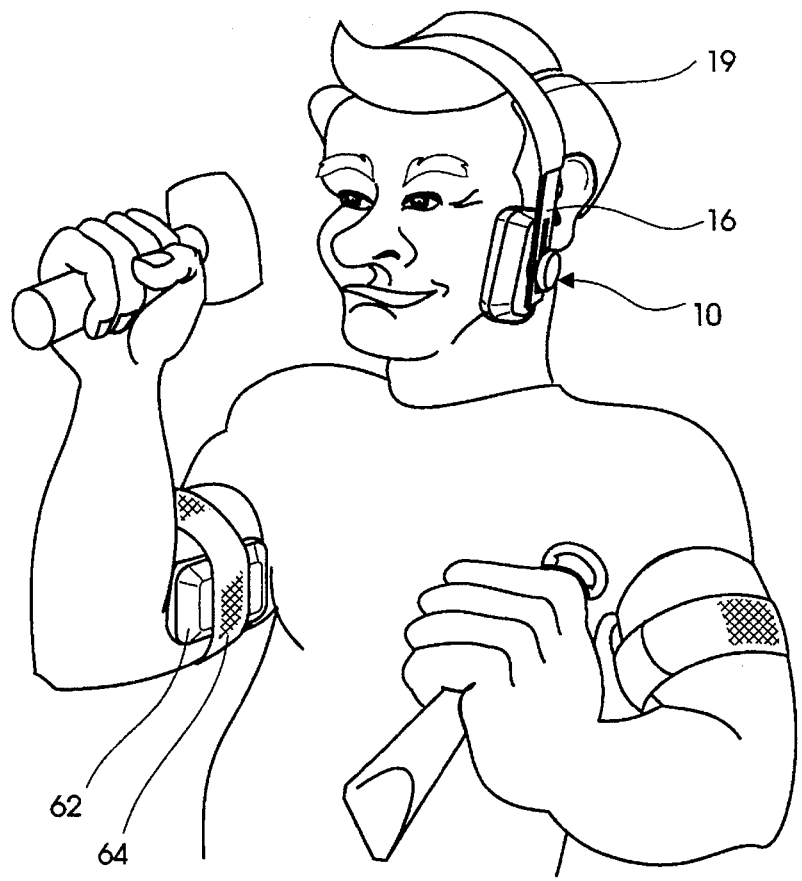
FIG. 1 shows the cold pack devices of the present invention in use.

Referring to the figures as shown in drawings, the cold pack device of the present invention is generally designated by the numeral 10. With reference to FIGS. 2–6, the cold pack device 10 includes a resilient headband 12, cold pack housings 14 slidably positionably fixably connected on headband ends 16 and which removably house cold packs 18. The headband 12 is generally u-shaped and configured to provide a pressure fit about the head and preferably includes a pad 19 surrounding part of the headband 12.

Each cold pack housing 14 includes an insulating member 20 which is preferably of a soft nature. Such insulation material might be Faultless® or Thinsulate®. Each cold pack housing 14 also includes a resilient inner member 22 connected to the member 20 and against which the cold pack 18 rests. The insulated member 20 is formed in a manner to have an opening periphery 24 forming an opening 26 therein. Surrounding the insulating member 22 and opening 26 is a cover portion 28 preferably made of a relatively thin skin hypoallergenic material resistant to leakage yet which significantly allows thermal transfer therethrough, such as a medical grade vinyl material. The cover 28 and insulating member 20 should be such as to enable adaptation to various contours of various individual faces. It is also contemplated that alternative designs could readily be made by those skilled in the art. For example, the cover 28 could be sealably connected to the inner member 22 with an air pocket therebetween to provide an insulating effect.

Formed through the cover 28 and the insulating member 20 and connecting to the resilient inner member 22 is a threaded housing 30. The resilient headband 12 has formed in its end 16 a slot 32. A thumb screw 34 is provided with a shaft 36 and a head 38, wherein the shaft is of a size to readily insert through the slot 32 and has formed a thread thereon to be complimentary received within the threaded housing 30. The head 38 is of a larger size than the slot 32 such that when the shaft 36 extends through the slot 32 and into the threaded housing 30, the thumb screw 34 can be tightened in a manner to fix the housing 14 at a desired position along the end 16.

Referring the embodiment shown in FIGS. 2–4, the resilient inner member 22 includes a spring-latch portion 40. Surrounding the spring-latch portion 40 is a cut out flap piece 42 of the insulating material 20 with a cut out complimentary piece 44 of the cover portion 28 which are removably held in place by a Velcro® attachment 46a and 46b affixed to portions 48 and 50 of cover 28. When disconnected as shown in FIG. 2, the spring-latch portion 40 can be pulled back to allow insertion and removal of cold pack 18 into and from housing 14, respectively.

Figure 5:
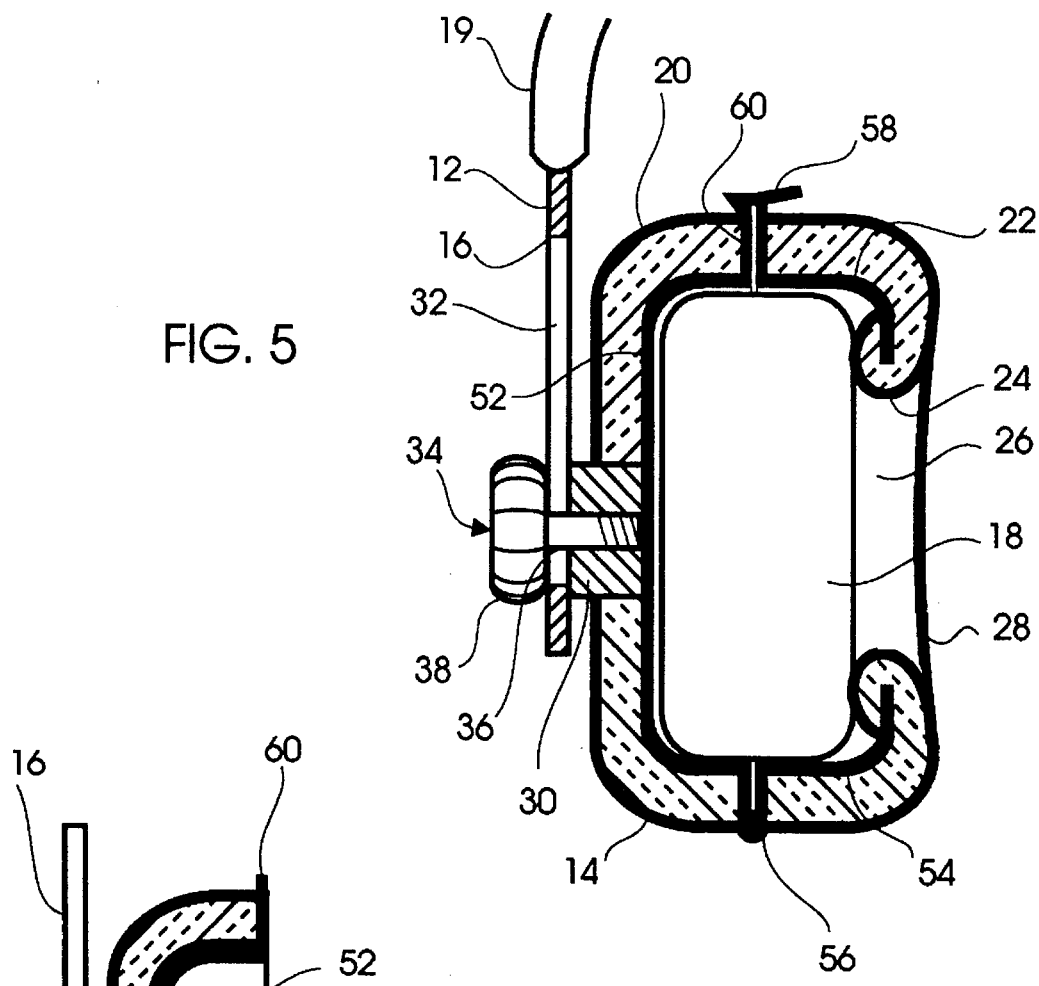
FIG. 5 is a cross-section of another embodiment of the cold pack device of the present invention.
Figure 6:
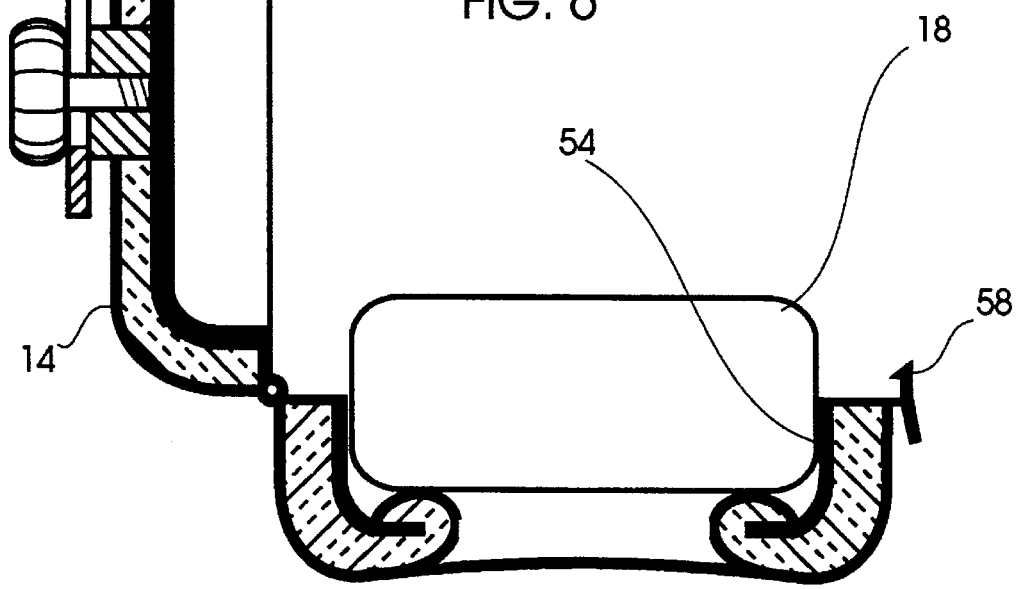
FIG. 6 is another cross-section of the other embodiment of the present invention showing an open position.

Referring to FIGS. 5–6, the housing 14 is clam shaped. The inner resilient member 22 includes pieces 52 and 54 which are hingedly connected together at hinge 56, wherein piece 54 which terminates in a latch 58 for latching onto an end 60 of piece 52.

Figure 7:
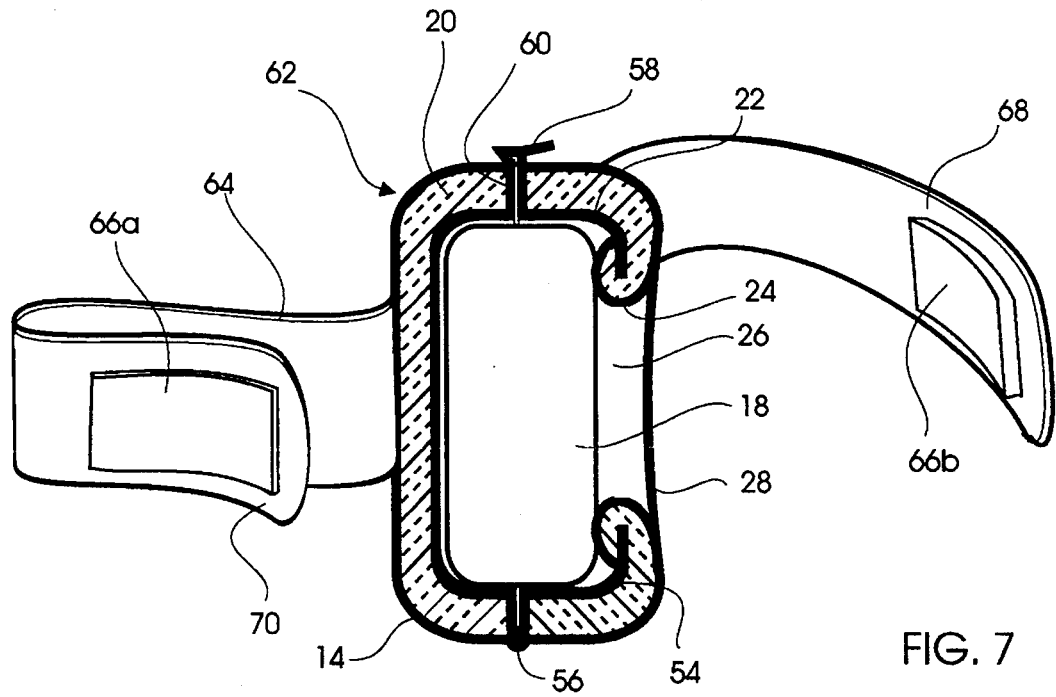
FIG. 7 is a cross-section of a part of yet another embodiment of the cold pack device of the present invention shown in FIG. 1.

Referring to FIG. 7, the housing 62 is essentially configured similar to that described above, with the exception of the band 64. Here, the band 64 is fixedly connected to housing 62 and is made of a flexible material, such as Nylon or the like. The band 64 has Velcro" attachments 66a and 66b on ends 68 and 70 to enable the housing 64 to be held against the arm.

The cold pack device shown in FIG. 7 can be used in conjunction with or separate from the device shown in FIGS. 2–6. Preferably, it is believed that maximum cooling can be achieved using minimal cooling devices through the use of both devices when worn as shown in FIG. 1.

The cold pack 18 is of a size and shape to be readily insertable within the housing 14 and can be made of any number of useful materials. For example, the casing may be of a suitable plastic type material and filled with Crylon™, Cryogel™ or water may be used.

While the invention has been disclosed with regard to the details of preferred embodiments discussed above, it is understood that the disclosure is intended to be illustrative only and not limiting in the claims appended hereto. It also contemplated that various modifications, derivations and improvements will be readily apparent to those skilled in the art and within the spirit of the invention and within the scope of the claims appended hereto.

What is claimed is:

1. A cold pack device for cooling a portion of a human body comprising:

a band member configured to encircle said body portion in a self-supporting manner;

a cold pack housing adjustably connected to the band member, having an outer layer for contacting the body portion and an inner layer, the cold pack housing defining an interior chamber containing a cold pack, the housing having an opening in a side extending through the outer and inner layers; the housing having a thickness such that the cold pack is recessed from the outer layer;

wherein when said band member encircles the body portion in a self-supporting manner, said outer layer contacts the body portion and said cold pack is maintained in a position spaced from said body portion, with said opening located between the cold pack and the body portion, thereby allowing thermal migration from said cold pack through said opening directly to said body portion.

2. The cold pack device of claim 1, wherein said band member is configured to fit about a human head.

3. The cold pack device of claim 2, which includes a plurality of said cold packs and a plurality of said housings positionably fixably connected to said band member.

4. The cold pack device of claim 3, wherein said housings are openable to readily permit disposal within said housing and removal from said housing of one of said cold packs.

5. The cold pack of claim 4, wherein each inner layer is a resilient member and has a portion connectably separable to effect insertion of the cold pack, wherein each housing further has an insulating layer substantially surrounding the cold pack.

6. The cold pack device of claim 1, wherein said band member is a flexible material and configured to fit about a human limb.

7. The cold pack device of claim 6, wherein said band member includes means for fastening one of its ends to another of its ends.

8. The cold pack device of claim 1, wherein said housing is slidably fixably connected to said band member.

9. The cold pack device of claim 1, wherein said housing includes an insulating member.

10. The cold pack device of claim 1, wherein said housing includes a resilient member configured to hold said cold pack.

11. The cold pack device of claim 1, wherein said housing is openable to readily permit disposal within said housing and removal from said housing of said cold pack.

12. The cold pack device of claim 1, which includes a plurality of said cold packs and a plurality of said housings positionably fixably connected to said band member.

13. A cold pack device for cooling a human head comprising:

a band member configured to encircle said head in a self-supporting manner;

a plurality cold pack housings adjustably connected to the band member, each housing having an outer layer for contacting the head an inner layer,and an interior chamber containing a cold pack, each housing having an opening in a side extending through the outer and inner layers and having a thickness such that the cold pack is recessed from the outer layer;

wherein when said band member encircles the head in a self-supporting manner, each housing is oriented such that the outer layer contacts head and said cold pack is maintained in a position spaced from said head, with said opening located between the cold pack and the head, thereby allowing thermal migration from said cold pack through said opening directly to said body portion.

14. The cold pack device of claim 13, wherein said housings are further characterized such that a portion of each said housing is openable to readily permit disposal within said housing and removal from said housing of one of said cold packs.

15. The cold pack of claim 4, wherein each inner layer is a resilient member and has a portion connectably separable to effect insertion of the cold pack, wherein each housing further has an insulating layer substantially surrounding the cold pack.

* * * * *